United States Patent
Hamasaki et al.

(10) Patent No.: US 9,315,799 B2
(45) Date of Patent: Apr. 19, 2016

(54) PROCESS FOR PREPARING PHOSPHATE COMPOUND BEARING ISOTOPE

(75) Inventors: Tomohiro Hamasaki, Fukuoka (JP); Tadaaki Ohgi, Fukuoka (JP)

(73) Assignee: BONAC Corporation, Kurume (JP)

( * ) Notice: Subject to any disclaimer, the term of this patent is extended or adjusted under 35 U.S.C. 154(b) by 56 days.

(21) Appl. No.: 14/116,763

(22) PCT Filed: May 7, 2012

(86) PCT No.: PCT/JP2012/061652
§ 371 (c)(1),
(2), (4) Date: Nov. 9, 2013

(87) PCT Pub. No.: WO2012/153704
PCT Pub. Date: Nov. 15, 2012

(65) Prior Publication Data
US 2014/0100362 A1    Apr. 10, 2014

(30) Foreign Application Priority Data
May 10, 2011    (JP) ................................. 2011-105722

(51) Int. Cl.
| | |
|---|---|
| *C07B 59/00* | (2006.01) |
| *C07F 9/06* | (2006.01) |
| *C07H 21/00* | (2006.01) |
| *C12N 15/10* | (2006.01) |
| *C07F 9/08* | (2006.01) |
| *C07F 9/09* | (2006.01) |

(52) U.S. Cl.
CPC ................ *C12N 15/10* (2013.01); *C07B 59/00* (2013.01); *C07B 59/005* (2013.01); *C07H 21/00* (2013.01); *C07F 9/06* (2013.01); *C07F 9/08* (2013.01); *C07F 9/09* (2013.01)

(58) Field of Classification Search
None
See application file for complete search history.

(56) References Cited

U.S. PATENT DOCUMENTS

| | | | |
|---|---|---|---|
| 5,003,097 A | | 3/1991 | Beaucage et al. |
| 5,177,198 A | * | 1/1993 | Spielvogel ............. C07H 21/00 536/122 |
| 6,017,700 A | * | 1/2000 | Horn et al. .................... 435/6.14 |
| 2009/0142849 A1 | * | 6/2009 | Yao ........................ C07B 59/008 436/86 |

OTHER PUBLICATIONS

Shaw, B. et al "Oligonucleoside boranophosphates" Chapter 11 from "Meth. Mol. Biol." S. Agrawal, ed. (1993) vol. 20, pp. 225-243.*
Culllis, P. et al "The mechanism of iodine-water oxidation . . . " JCS Chem. Comm. (1992) pp. 1207-1208.*
Iyer, R. et al "The automated synthesis of sulfur-containing oligodeoxyribonucleotides . . . " J. Org. Chem. (1990) vol. 55, pp. 4693-4699.*
Bentrude et al., *Journal of the American Chemical Society*, 111(11): 3981-3987 (1989).
Broeders et al., *Journal of the American Chemical Society*, 114: 9624-9633 (1992).
Sopchik et al., *Tetrahedron Letters*, 30(10): 1221-1224 (1989).
European Patent Office, Extended European Search Report in European Patent Application No. 12782845.7 (Sep. 15, 2014).
Dai et al., "Efficient Synthesis of [2"18-O] Uridine and Its Incorporation into Oligonucleotides: A New Tool for Mechanistic Study of Nucleotidyl Transfer Reactions by Isotope Effect Analysis," Journal of Organic Chemistry, 73: 309-311 (2008).
Stec et al., "Automated Solid-Phase Synthesis, Separation, and Stereochemistry of Phosphorothioate Analogues of Oligodeoxyribonucleotides," Journal of the American Chemical Society, 106: 6077-6079 (1984).
Higson et al., "Synthesis of an Oligothymidylate Containing Boranophosphate Linkages," Tetrahedron Letters, 39: 3899-3902 (1998).
International Search Report issued in corresponding International Patent Application No. PCT/JP2012/061652 dated Jun. 12, 2012.

* cited by examiner

*Primary Examiner* — Leigh C Maier
(74) *Attorney, Agent, or Firm* — Leydig, Voit & Mayer, Ltd.

(57) ABSTRACT

The present invention provides a process for preparing an isotope-containing phosphate compound easily. The process for preparing an isotope-containing phosphate compound according to the present invention includes the step of: oxidizing a trivalent phosphorus compound with an oxidizing agent containing an isotope to synthesize a pentavalent phosphate compound to which the isotope has been introduced. The present invention preferably is applied to the synthesis of nucleic acids such as DNA and RNA, for example. The isotope preferably is a stable isotope. The oxidizing agent preferably is $H_2{}^{18}O$, 3H-1,2-benzodithiol 3-one 1,1-dioxide having $^{34}S$, or a diisopropylethylamine-borane complex having $^{10}B$, for example.

13 Claims, 5 Drawing Sheets

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial
<220> FEATURE:
<223> OTHER INFORMATION: siRNA

<400> SEQUENCE: 1
ccaugagaag uaugacaaca g                                                  21

<210> SEQ ID NO 2
<211> LENGTH: 21
<212> TYPE: RNA
<213> ORGANISM: Artificial
<220> FEATURE:
<223> OTHER INFORMATION: siRNA

<400> SEQUENCE: 2
guugucauac uucucauggu u                                                  21

<210> SEQ ID NO 3
<211> LENGTH: 21
<212> TYPE: RNA
<213> ORGANISM: Artificial
<220> FEATURE:
<223> OTHER INFORMATION: siRNA

<400> SEQUENCE: 3
uacuauucga cacgcgaagu u                                                  21

<210> SEQ ID NO 4
<211> LENGTH: 21
<212> TYPE: RNA
<213> ORGANISM: Artificial
<220> FEATURE:
<223> OTHER INFORMATION: siRNA

<400> SEQUENCE: 4
cuucgcgugu cgaauaguau u                                                  21

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
ggagaaggct ggggctcatt tgc                                                23

<210> SEQ ID NO 6
```

```
<211> LENGTH: 23
<212> TYPE: DNA
<213> ORGANISM: Artificial
<220> FEATURE:
<223> OTHER INFORMATION: primer

<400> SEQUENCE: 6
tggccagggg tgctaagcag ttg                                              23

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
gccacggctg cttccagctc ctc                                              23

<210> SEQ ID NO 8
<211> LENGTH: 25
<212> TYPE: DNA
<213> ORGANISM: Artificial
<220> FEATURE:
<223> OTHER INFORMATION: primer

<400> SEQUENCE: 8
aggtctttgc ggatgtccac gtcac                                            25
```

PROCESS FOR PREPARING PHOSPHATE COMPOUND BEARING ISOTOPE

A computer readable text file, entitled "SequenceListing.txt," created on or about Oct. 24, 2013 with a file size of about 2 kb contains the sequence listing for this application and is hereby incorporated by reference in its entirety.

TECHNICAL FIELD

The present invention relates to a process for preparing an isotope-containing phosphate compound.

BACKGROUND ART

A method generally used for examining the behavior of a compound in vivo is using the compound labeled with an isotope(s) introduced thereto. Examples of the compound include nucleic acids such as DNA and RNA. As the isotope, the use of a stable isotope brings an attention because it does not affect living organisms.

In particular, synthesis of a nucleic acid having stable isotopes introduced thereto generally is carried out by introducing a stable isotope to a monomer beforehand, and then, synthesizing a polynucleotide using this monomer as a raw material. In order to detect the stable isotopes with high sensitivity, it is desirable that the polynucleotide contains a large number of stable isotopes. However, according to this method, in order to introduce a large number of stable isotopes, all the monomers having bases A, G, C, and T/U, respectively, need to be labeled with the stable isotopes. Thus, this method has a problem in that it requires a large amount of labor and cost.

As a method for introducing a stable isotope, there has been disclosed a method in which the ring in 2,2'-cyclouridine is opened with benzoic acid ($PhC^{18}O_2H$), and a hydroxy group having a stable isotope ($—^{18}OH$) is introduced to the 2'-position of the sugar (Non-Patent Document 1). However, according to this method, it is only possible to label a nucleoside having a specific pyrimidine base, and nucleosides having other bases cannot be obtained.

The above-described problem in terms of labor and cost in labeling with a stable isotope occurs not only in labeling the nucleic acids but also in labeling low molecular weight compounds, such as pharmaceuticals and agricultural chemicals, for example.

CITATION LIST

Non-Patent Document(s)

[Non-Patent Document 1] J. Org. Chem. 2008 Jan. 4; 73(1): pp. 309-311

BRIEF SUMMARY OF THE INVENTION

With the foregoing in mind, one object of the present invention is to provide a process for preparing an isotope-containing phosphate compound easily.

In order to achieve the above object, the present invention provides a process for preparing an isotope-containing phosphate compound including the step of: oxidizing a trivalent phosphorus compound with an oxidizing agent containing an isotope to synthesize a pentavalent phosphate compound to which the isotope has been introduced.

According to the preparation process of the present invention, an isotope-containing phosphate compound can be prepared easily merely by using the oxidizing agent containing the isotope. The preparation process of the present invention is useful in, for example, synthesis of nucleic acids having a phosphate group(s) and synthesis of low molecular weight compounds having a phosphate group(s), such as agricultural chemicals, pharmaceuticals, and phospholipids.

MODE FOR CARRYING OUT THE INVENTION

Figure 1:
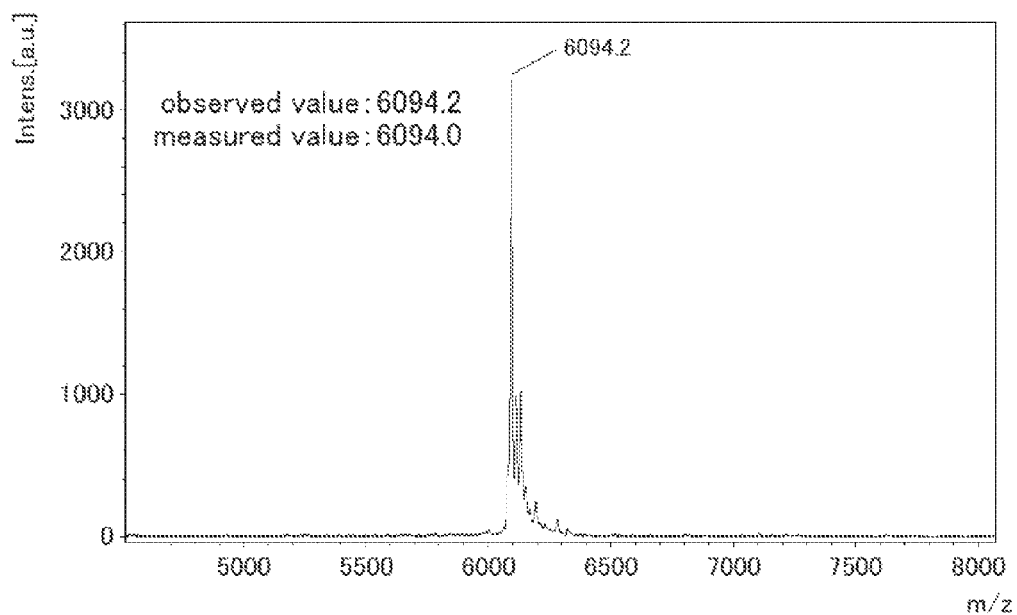
FIG. 1 is a mass spectrometry chromatogram of a $^{18}O$-labeled poly(U) obtained in Example 1.

As described above, the process for preparing an isotope-containing phosphate compound according to the present invention is characterized in that it includes the step of oxidizing a trivalent phosphorus compound with an oxidizing agent containing an isotope (hereinafter referred to as "isotope oxidizing agent") to synthesize a pentavalent phosphate compound to which the isotope has been introduced.

According to the preparation process of the present invention, the isotope oxidizing agent oxidizes trivalent phosphorus in the trivalent phosphorus compound to pentavalent phosphorus, and the isotope derived from the isotope oxidizing agent then binds to the pentavalent phosphorus. Thus, merely by causing an oxidation reaction with the isotope oxidizing agent, it is possible to obtain an isotope-containing pentavalent phosphate compound. Therefore, it can be said that the present invention can further broaden the use of isotope-containing phosphate compounds, for example.

As described above, the present invention is characterized in oxidizing a trivalent phosphorus compound with the isotope oxidizing agent, and other configurations and conditions are not particularly limited.

As described above, the preparation process according to the present invention preferably is applied to, for example: synthesis of phosphate group-containing agricultural chemicals, pharmaceuticals, phospholipids etc.; and synthesis of phosphate group-containing nucleic acids such as RNA and DNA and monomers such as nucleoside-monophosphate, nucleoside-diphosphate, and nucleoside-triphosphate. Among them, it is particularly preferable to apply the preparation process of the present invention to the synthesis of the nucleic acids. The method for synthesizing the nucleic acids is by no means limited, and examples thereof include a phosphite method and a phosphoamidite method (also referred to as a "phosphoramidite method") (hereinafter referred to as an "amidite method"). The amidite method will be described below with reference to an illustrative example. It is to be noted, however, that the present invention is not limited thereto. In solid phase synthesis of a nucleic acid, the amidite method generally is carried out by repeating a cycle of treatment until a nucleic acid with a desired length is obtained, with the following three step being defined as one cycle: a monomer amidite coupling step; an oxidation step of oxidizing trivalent phosphorus generated by the monomer amidite coupling step to pentavalent phosphorus (a phosphate group); and a deprotection step of removing a protecting group from the sugar at the 5' end. According to the present invention, it is possible to introduce isotopes to phosphate groups in the phosphodiester bonds easily merely by using the isotope oxidizing agent in the oxidation steps. Also, by using the isotope oxidizing agent only in the oxidation step in a desired cycle, it is possible to introduce the isotope only to a desired phosphodiester bond. Furthermore, by using the isotope oxidizing agent in the oxidation step in every cycle, it is also possible to introduce the isotope to a phosphate group in every phosphodiester bond. As described above, according to the conventional method, it is necessary to synthesize an amidite having an isotope introduced thereto for each one of bases to be labeled, and thus there is a problem in that it requires labor and cost. However, according to the present invention, an isotope is introduced to a phosphate group in the phosphodiester bond regardless of the type of base. Thus, it is not necessary to synthesize an amidite having an isotope introduced thereto separately for each base as described above. Therefore, the preparation process according to the present invention can reduce the labor and cost greatly, and the process is not affected by the base sequence of a nucleic acid to be synthesized.

In the present invention, the oxidation reaction caused by the oxidizing agent is such that, for example, trivalent phosphorus in the trivalent phosphorus compound is oxidized to pentavalent phosphorus and an atom derived from the oxidizing agent then binds to the pentavalent phosphorus. Thus, in the present invention, the isotope oxidizing agent may be such that the atom binding to the pentavalent phosphorus is the isotope.

In the present invention, the isotope oxidizing agent is not particularly limited, as long as it serves to oxidize trivalent phosphorus in the trivalent phosphorus compound to pentavalent phosphorus and to supply an atom to the pentavalent phosphorus, and has an isotope as the atom to be supplied to the pentavalent phosphorus, for example. Oxidizing agents that cause such an oxidation reaction are known to those skilled in the art based on common general technical knowledge at the time the application was filed. Also, as oxidizing agents having an isotope as the atom to be supplied, it is possible to obtain commercially available products, or they can be prepared based on common general technical knowledge at the time the application was filed, for example.

The isotope is not particularly limited. It may be, for example, a stable isotope or a radioisotope, and preferably is the former. The stable isotope offers a little risk of radiation exposure, and requires no dedicated facility, for example. Thus, the stable isotope is excellent in handleability and can reduce the cost. Moreover, unlike a fluorescent label, the stable isotope does not change the physical properties of a compound labeled therewith, and thus is excellent as a tracer, for example.

The isotope oxidizing agent is not particularly limited, and may be an oxygen donor that supplies an oxygen isotope to pentavalent phosphorus by oxidation, for example. The isotope may be, for example, $^{17}O$, $^{18}O$, or the like, and preferably is $^{18}O$.

The oxygen donor may be, for example, water or a peroxide having an oxygen isotope. The peroxide is represented by, for example, the chemical formula R—O—O—R', where R and R' are each H or any substituent, for example. R and R' may be the same or different from each other. The substituent is not particularly limited. Examples of the substituent include alkyl groups with 1 to 10 carbon atoms, which may be straight or branched. Examples of the alkyl groups include butyl groups, such as a t-butyl group. The peroxide preferably is the one where at least one of R and R' is hydrogen, halogen, or a univalent metal, for example, and more preferably is a hydroperoxide where at least one of R and R' is hydrogen. Examples of the hydroperoxide include t-butyl hydroperoxide. The univalent metal may be, for example, an alkali metal, examples of which include sodium, potassium, lithium, rubidium, cesium, and francium.

Above all, it is particularly preferable that the oxygen donor is $H_2^{18}O$ having $^{18}O$, because, for example, commercially available products with high purity are available. When the water having an oxygen isotope is used, it is preferable that iodine ($I_2$), pyridine (Py), and tetrahydrofuran (THF) also are used in combination, for example. When the water having an oxygen isotope is used, a pentavalent phosphate compound to be obtained preferably is such that, for example, a hydroxy group having the oxygen isotope (—$^{18}OH$) is bound to pentavalent phosphorus, and hydrogen in the hydroxy group may be substituted with a univalent metal, such as an alkali metal, for example. Examples of the alkali metal include sodium, potassium, lithium, rubidium, cesium, and francium.

Another example of the isotope oxidizing agent is a sulfur donor that supplies a sulfur isotope to pentavalent phosphorus by oxidation. The isotope may be, for example, $^{33}S$, $^{34}S$, $^{36}S$, or the like, and preferably is $^{34}S$.

For example, the sulfur donor preferably is a disulfide (a compound having —S—S—) having a sulfur isotope, more preferably an organic disulfide, and still more preferably a cyclic organic disulfide. Specific examples of the disulfide include 3H-1,2-benzothiol 3-one 1,1-dioxide and 5-((dimethylamino-methylidene)amino)-3H-1,2,4-dithiazole-3-thione. The disulfide preferably is 3H-1,2-benzodithiol 3-one 1,1-dioxide, more preferably 3H-1,2-benzodithiol 3-one 1,1-dioxide having $^{34}S$. When the sulfur donor having a sulfur isotope is used, a pentavalent phosphate compound to be obtained preferably is such that, for example, the sulfur isotope is bound to pentavalent phosphorus. Specifically, it is preferable that the pentavalent phosphate compound forms phosphorothioate.

Still another example of the isotope oxidizing agent is a boron donor that supplies a boron isotope to pentavalent phosphorus by oxidation. The isotope may be $^{10}B$ or the like, for example.

For example, the boron donor preferably is an amine-borane complex having a boron isotope, more preferably a trialkylamine-borane complex having a boron isotope. Examples of the trialkylamine-borane complex include a diisopropylethylamine (DIPEA)-borane complex represented by $C_8H_{19}N$—$BH_3$. Preferably, the trialkylamine-borane complex is a DIPEA-borane complex having $^{10}B$, which is represented by $C_8H_{19}N$—$^{10}BH_3$. When the DIPEA-borane complex having a boron isotope is used, a pentavalent phosphate compound to be obtained preferably is such that, for example, a borane group (—$^{10}BH3$-) having the boron isotope is bound to pentavalent phosphorus. Specifically, it is preferable that the pentavalent phosphate compound forms boranophosphate. In the amine-borane complex, hydrogen in the borane group may be substituted with halogen, for example. Examples of the halogen include F, Cl, Br, and I. Furthermore, the borane group may form a salt with a univalent metal or a divalent metal, for example. The univalent metal may be, for example, an alkali metal, examples of which include sodium, potassium, lithium, rubidium, cesium, and francium. The divalent metal may be, for example, an alkaline-earth metal, examples of which include calcium, strontium, barium, and radium.

In the present invention, the trivalent phosphorus compound is not particularly limited as long as it is a compound having trivalent phosphorus.

The trivalent phosphorus compound may be phosphorous acid or a phosphorous ester, for example.

The phosphorous acid encompasses, in addition to the phosphorous acid [$HP(O)(OH)_2$], salts and derivatives of the phosphorous acid. According to the preparation process of the present invention, by using the phosphorous acid as the trivalent phosphorus compound, it is possible to prepare a phosphoric acid in which an isotope is bound to phosphorus. The phosphoric acid to be obtained encompasses salts and derivatives of the phosphoric acid, for example.

The phosphorous ester may be any of a phosphorous monoester [$R^1O—P(OX^2)—OX^3$], a phosphorous diester [$R^1O—P(OR^2)—OX^3$], and a phosphorous triester [$R^1O—P(OR^2)—OR^3$], for example. Each of $X^2$ and $X^3$ is hydrogen or a univalent metal, for example. The univalent metal may be, for example, an alkali metal, examples of which include sodium, potassium, lithium, rubidium, cesium, and francium. $R^1$, $R^2$, and $R^3$ are by no means limited, and examples thereof include various organic groups, such as hydrocarbon groups to be described below. By using the phosphorous ester as the trivalent phosphorus compound, it is possible to prepare a phosphoric ester in which an isotope is bound to phosphorus.

When the pentavalent phosphate compound synthesized by the preparation process of the present invention is the nucleic acid, the nucleic acid may be a monomer or a polymer obtained by the polymerization of the monomer, for example.

The monomer may be a nucleotide constituting RNA or DNA, for example. The structure of the nucleotide is such that, for example, a pentavalent phosphate group is bound to a nucleoside composed of a sugar and a base. More specifically, the nucleotide contains a sugar, a base, and a pentavalent phosphate group, with the base being bound to the 1'-position of the sugar and the pentavalent phosphate group being bound to the 5'-, 3'-, or 2'-position of the sugar. Specific examples of the nucleotide include ribonucleotide and deoxyribonucleotide. The term "nucleotide" encompasses derivatives of the nucleotide, for example. The above-described polymer is, for example, a polymer of the nucleotides, and specific examples of the polymer include RNA as a polymer of ribonucleotides, DNA as a polymer of deoxyribonucleotides, and a polymer of ribonucleotides and deoxyribonucleotides (a DNA/RNA chimera). In the polymer, for example, the number of the monomer to be polymerized is not limited, and the term "polymer" encompasses oligomers. In the polymer, for example, a sugar of one of adjacent nucleotides is bound to a sugar of another nucleotide via the phosphate group. More specifically, for example, it is preferable that, between the nucleotide residues, the 5'-, 3'-, or 2'-position of one of the sugars is bound to the 5'-, 3'-, or 2'-position of the other sugar via the phosphate group. The combination of the binding site in the sugar of one of the nucleotides and the binding site in the sugar of another nucleotide is not particularly limited, and examples thereof include: the combination of the 5'-position and the 3'-position; the combination of the 5'-position and the 5'-position; the combination of the 3'-position and the 3'-position; and the combination of the 2'-position and the 5'-position.

In the nucleotide, the sugar may be a ribose in which a hydroxy group is bound to a carbon atom at the 2'-position, or may be a deoxyribose in which a hydrogen atom is bound to a carbon atom at the 2'-position, for example. In the ribose, the hydroxy group may be substituted (modified) with any atom or group, for example. The atom may be a hydrogen atom or a halogen atom, for example. Examples of the halogen atom include F, Cl, Br, and I. Among them, F (fluorine atom) is preferable. The group may be, for example, an alkoxy group (—O— alkyl group), an acyloxy group (—O— acyl group), an amino group ($NH_2$ group), or a substituted amino group obtained by substituting H in the amino group with a substituent. The alkoxy group (—O— alkyl group) is not particularly limited. Examples of the alkoxy group include a methoxy group (—O— Me group), and the alkyl group is not limited. The acyloxy group (—O— acyl group) is not particularly limited. Examples of the acyloxy group include a —O—CHO group, and the alkyl group is not limited. In the deoxyribose, the hydrogen atom may be substituted (modified) with any atom, for example. Examples of the atom include the above-described halogen atoms.

The base is not particularly limited, and examples thereof include adenine, guanine, cytosine, thymine, and uracil. Other examples of the base include, as substituted bases obtained through substitution in these bases: 7-deazaguanine, 7-deaza-8-azaguanine, 5-propynylcytosine, 5-propynyluracil, 7-deazaadenine, 7-deaza-8-azaadenine, 7-deaza-6-oxopurine, 6-oxopurine, 3-deazadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-aminopurine, 5-fluorouracil, 2,6-diaminopurine, 8-aminopurine, 4-triazolo-5-methylthymine, 4-triazolo-5-methyluracil, and hypoxanthine. The base may be a natural base or an unnatural base, for example.

Preparation of the monomer having the isotope introduced thereto may be achieved by oxidizing, as the trivalent phosphorus compound, a nucleoside having the trivalent phosphorus with the isotope oxidizing agent, for example. According to this method, the trivalent phosphorus bound to the nucleoside is oxidized to be the pentavalent phosphorus, and an isotope derived from the isotope oxidizing agent binds to the pentavalent phosphorus. Thus, a monomer having the isotope can be obtained.

It is preferable that the nucleoside having the trivalent phosphorus contains a sugar and a base, with the base being bound to the 1'-position of the sugar and the trivalent phosphorus being bound to the sugar, for example. It is more preferable that the trivalent phosphorus is bound to the 5'-, 3'-, or 2'-position of the sugar.

As described above, the nucleoside having trivalent phosphorus is, for example, the phosphorous ester, which specifically can be any of a phosphorous monoester [$R^1O—P(OX^2)—OX^3$], a phosphorous diester [$R^1O—P(OR^2)—OX^3$], and a phosphorous triester [$R^1O—P(OR^2)—OR^3$]. It is preferable that any one of $R^1$, $R^2$, and $R^3$ is the nucleoside.

Examples of the process for preparing the polymer having the isotope introduced thereto include the following first process and second process.

In the first process, for example, a previously synthesized polymer containing nucleoside residues each having trivalent phosphorus is used as the trivalent phosphorus compound, and this polymer is oxidized with the isotope oxidizing agent, whereby an isotope is introduced to the polymer. According to this method, the trivalent phosphorus in the polymer turns to the pentavalent phosphorus by oxidation, and the isotope derived from the isotope oxidizing agent binds to the pentavalent phosphorus. In this manner, the polymer having the isotope can be obtained.

The polymer having the trivalent phosphorus contains two or more nucleoside residues. Each of the nucleoside residues contains a sugar and a base, with the base bound to the 1'-position of the sugar. Between the nucleoside residues, the sugars of the respective nucleoside residues are bound to each other via phosphorus. More specifically, for example, it is preferable that, between the nucleoside residues, the 5'-, 3'-, or 2'-position of one of the sugars is bound to the 5'-, 3'-, or 2'-position of the other sugar via the phosphorus. The combination of the binding site in the sugar of one of the nucleotides and the binding site in the sugar of the other nucleotide is not particularly limited, and examples thereof include: the combination of the 5'-position and the 3'-position; the combination of the 5'-position and the 5'-position; the combination of the 3'-position and the 3'-position; and the combination of the 2'-position and the 5'-position. The phosphorus between at least one pair of adjacent nucleoside residues is the trivalent phosphorus. In the above-described polymer, for example, phosphorus between at least one pair of adjacent nucleoside residues may be trivalent phosphorus, or phosphorus between every pair of adjacent nucleoside residues may be trivalent phosphorus. In the former case, only the trivalent phosphorus in the polymer is oxidized to pentavalent phosphorus, and the isotope derived from the isotope oxidizing agent is introduced to the pentavalent phosphorus. In the latter case, the trivalent phosphorus between every pair of adjacent nucleoside residues is oxidized to pentavalent phosphorus, and the isotope derived from the isotope oxidizing agent is introduced to the pentavalent phosphorus.

The trivalent phosphorus compound is, for example, the phosphorous ester, as described above. The phosphorous ester can be either of a phosphorous diester [$R^1O$—$P(OR^2)$—$OX^3$] and a phosphorous triester [$R^1O$—$P(OR^2)$—$OR^3$], for example. It is preferable that $R^1$ and $R^2$ are each the nucleoside residue or a polymer of the nucleoside residues, and they may be the same or different from each other. When $R^1$ and/or $R^2$ is a polymer of the nucleoside residues, the polymer may be, for example, a polymer (polynucleotide) in which the nucleotide residues are bound to each other by phosphodiester bond, or may be a polymer in which the nucleotide residues are bound to each other via trivalent phosphorus. The number of nucleotide residues composing the polymer is not limited.

The second process is a process that performs coupling of nucleosides and then achieves isotope introduction by oxidation using the isotope oxidizing agent, for example. According to this process, it is possible to synthesize a polymer having an isotope by introducing the isotope to pentavalent phosphorus between any desired pair of adjacent nucleoside residues. The method for synthesizing the polymer is not particularly limited, and examples thereof include a phosphite method and an amidite method. These synthesis methods are not particularly limited, and may be either solid phase synthesis or liquid phase synthesis, for example.

More specifically, the second process is, for example, the preparation process according to the present invention further including a coupling step of coupling two molecules of monomers each containing a nucleoside to synthesize the trivalent phosphorus compound, wherein, in the oxidation step, the trivalent phosphorus compound obtained by the coupling step is oxidized with the isotope oxidizing agent to synthesize a pentavalent phosphate compound to which the isotope has been introduced.

The kind of the monomer is not particularly limited, and any known monomer can be used. One of the monomers preferably is such that, for example, in the sugar of the nucleoside, trivalent phosphorus is bound to a site binding to the other monomer, and to any other site having a hydroxy group, a protecting group for protecting the hydroxy group is bound. The site to which the trivalent phosphorus is bound is not particularly limited, and may be the 5'-, 3'-, or 2'-position. The site to which the protecting group is bound is not particularly limited, and may be the 5'-, 3'-, or 2'-position. The combination of the binding site of the trivalent phosphorus and the binding site of the protecting group is not particularly limited, and examples thereof include: the combination of the 5'-position and the 3'-position; the combination of the 5'-position and the 5'-position; the combination of the 3'-position and the 3'-position; and the combination of the 2'-position and the 5'-position. As a specific example, one of the monomers preferably is such that, for example, trivalent phosphorus is bound to the 3'-position of the sugar of the nucleoside, and a protecting group for a hydroxy group is bound to the 5'-position of the sugar. Preferably, the trivalent phosphorus has a reaction group that reacts with a hydroxy group. The protecting group is not particularly limited, and may be a dimethoxytrityl (DMTr) group or the like, for example.

The other monomer preferably is such that, in the sugar of the nucleoside, the site binding to the above-described monomer is a hydroxy group from which the protecting group has been removed. The site binding to the above-described monomer is not particularly limited, and may be the 5'-, 3'-, or 2'-position. As a specific example, the other monomer preferably is such that the 5'-position of the sugar of the nucleoside is a hydroxy group from which the protecting group has been removed. When the two molecules of monomers are coupled in the coupling step, the reaction group (e.g., the 3'-position) of the former reacts with the hydroxy group (e.g., 5'-position) in the sugar of the latter, whereby the monomers are bound to each other via the trivalent phosphorus. By oxidizing the trivalent phosphorus between the monomers with the isotope oxidizing agent, the trivalent phosphorus is oxidized to pentavalent phosphorus, whereby a polymer in which the nucleosides are bound to each other by phosphodiester bond having the isotope is synthesized.

The monomer having the protecting group bound thereto is not particularly limited, and examples of applicable monomers include those used in the above-described phosphite method, amidite method, etc. Examples of the monomers used in the amidite method include known phosphoroamidites, and specific examples thereof include TBDMS-amidite, TOM-amidite, and ACE-amidite.

The nucleoside is not particularly limited, and similarly to the above-described nucleoside, it contains a sugar and a base, with the base being bound to the 1'-position of the sugar. In the case of solid phase synthesis, it is preferable that the latter monomer is immobilized on the solid phase at a site other than the binding site to the former monomer, for example. As a specific example, when the latter monomer is, e.g., a monomer in which the 5'-position of the sugar is a hydroxy group, the 3'-position of the sugar preferably is immobilized on the solid phase, for example.

The second process may further include, for example, a deprotection step of removing the protecting group (e.g., 5'-position) in the sugar of the nucleoside. The deprotection method is not particularly limited, and the deprotection can be achieved by, for example, a known method selected depending on the kind of the protecting group.

The second process may be configured so as to perform the coupling of nucleosides and the isotope introduction by oxidation using the isotope oxidizing agent repeatedly. Specifically, the second process may be such that it further includes a coupling step of coupling another monomer containing a nucleoside to the pentavalent phosphate compound to synthesize a trivalent phosphorus compound, and the trivalent phosphorus compound obtained by the coupling step is oxidized with the isotope oxidizing agent to synthesize a pentavalent phosphate compound to which the isotope has been introduced.

By repeating the coupling step and the oxidation step with the isotope oxidizing agent being used in a desired oxidation step(s) or in all the oxidation steps, it is possible to introduce an isotope to a desired phosphodiester bond(s).

At the time of coupling another monomer to the pentavalent phosphate compound, it is preferable that, for example, the monomer is coupled after the pentavalent phosphate compound has been subjected to deprotection so as to remove a protecting group (e.g., 5'-position) in the sugar of the nucleoside at the 5' end. That is, in the second process, it is preferable to perform the coupling step, the oxidation step, and the deprotection step repeatedly. The number of times these steps are repeated is by no means limited, and they may be repeated until a desired polymer length is obtained.

Examples of a reaction for introducing an isotope to a nucleic acid using an isotope oxidizing agent having the isotope are shown below. It is to be noted, however, that the present invention is not limited to these illustrative examples. In the following formulae, R at the 2'-position of the sugar is not particularly limited, and examples thereof include the above-described hydrocarbon groups. As shown in the following formulae, for example, by oxidization with $I_2$/Py/$H_2{}^{18}O$, —$^{18}OH$ can be introduced to a phosphate group; by oxidization with 3H-1,2-benzodithiol 3-one 1,1-dioxide having $^{34}S$, —$^{34}S^-$ can be introduced to a phosphate group; and by oxidization with a DIPEA-borane complex, —$^{10}BH_3{}^-$ can be introduced to a phosphate group.

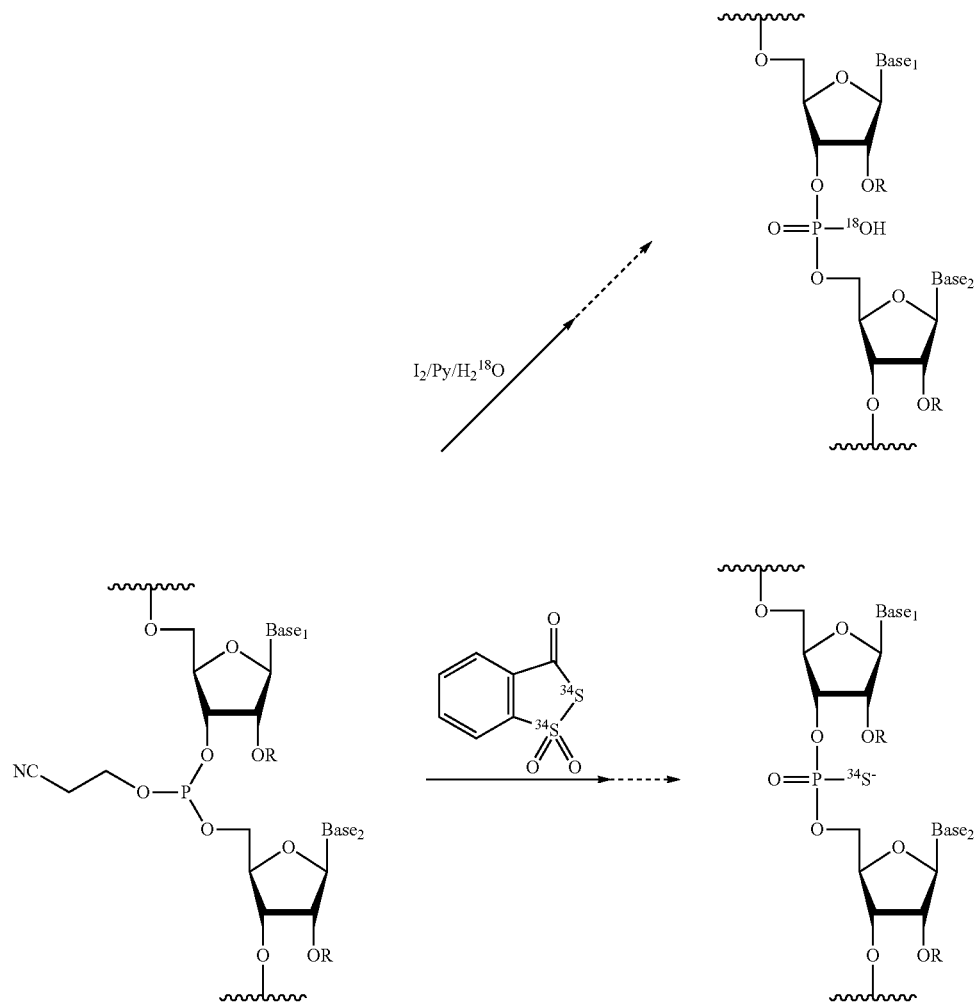

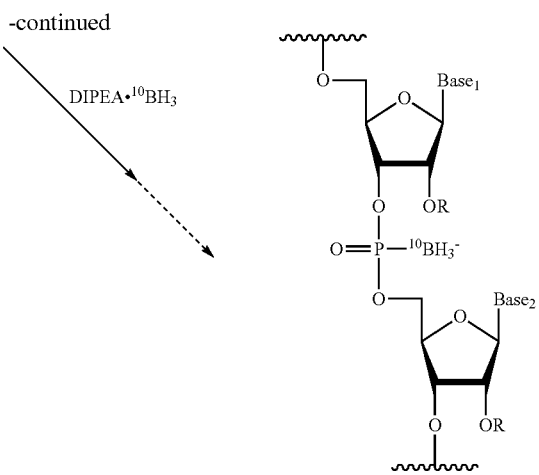

According to the preparation process of the present invention, it is also possible to prepare an agricultural chemical, a pharmaceutical, a phospholipid, or the like, in which an isotope(s) has been introduced to a phosphate group(s), for example. Examples of the agricultural chemical include malathion and sumithion. Examples of the pharmaceutical include hydrocortisone sodium phosphate (trade name: CLEITON).

Shown below is an example of a reaction for synthesizing a low-molecular phosphate compound in which an isotope has been introduced to a phosphate group using alcohol as a starting material. It is to be noted, however, that the present invention is not limited thereto. In the following scheme (1), R is by no means limited, and may be any of the above-described hydrocarbon groups, for example. First, in Reaction 1, R—OH reacts with a trivalent phosphorus donor, whereby a trivalent phosphorus compound is synthesized. The trivalent phosphorus donor is not particularly limited, and may be a compound having a cyano group as shown below, examples of which include N,N-diisopropylamino cyanoethyl phosphonamidic chloride and 2-cyanoethyl N,N,N,N-tetraisopropyl phosphane. Then, by causing Reaction 2 using the above-described isotope oxidizing agent, a pentavalent phosphate compound in which the isotope has been introduced to X is obtained. As the isotope oxidizing agent, it is preferable to use, for example: the oxygen donor when an oxygen isotope is to be introduced to X; the sulfur donor when a sulfur isotope is to be introduced to X; and the boron donor when a boron isotope is to be introduced to X.

The isotope-containing phosphate compound obtained by the preparation process of the present invention can be used as an alternative to a conventional phosphate compound, for example, and the use thereof is by no means limited.

EXAMPLES

Next, the present invention will be described with reference to examples. It is to be noted, however, that the present invention is by no means limited or restricted by the following examples.

Example 1

(1) Synthesis of RNA Labeled with $^{18}O$

As a synthesized RNA, a 20-mer $^{18}O$-labeled poly(U) in which a single $^{18}O$ atom had been introduced to each of phosphate groups in the phosphodiester bonds was synthesized. As a monomeric raw material, TBDMS-amidite was used, and with the use of a nucleic acid synthesis system (trade name: ABI Expedite 8909, manufactured by ABI), 19 cycles of treatment were performed based on the phosphoramidite method, with a coupling step, an oxidation step, and a deprotection step of removing a protecting group (a dimethoxytrityl (DMTr) group) at the 5'-position of a ribose residue being defined as one cycle. In every oxidation step, a composition containing $H_2{}^{18}O$ having an oxygen isotope $^{18}O$ (WATER-$^{18}O$, the purity of $^{18}O$: atom %=99.2%, TAIYO NIPPON SANSO CORPORATION) was used as an isotope oxidizing agent. As the composition, a mixture of THF, pyridine, and water, containing 0.1 mol/l iodine was used. In the mixture, the mixing ratio (volume ratio) of THF:pyridine:water was set to 78:20:2. The synthesis was carried out according to the usual method, except that the composition containing $H_2{}^{18}O$ was used.

(2) Molecular Weight Measurement

The molecular weight of the thus-obtained $^{18}O$-labeled poly(U) was measured using a matrix assisted laser desorption ionization time-of-flight mass spectrometer (trade name: Bruker AUTOFLEX), based on the usual method.

The analysis result is shown in FIG. 1. FIG. 1 is a chromatogram showing the result of mass spectrometry with respect to the synthesized RNA. The observed value of the $^{18}O$-labeled poly(U) was 6094.2.

As described above, the $^{18}$O-labeled poly(U) was obtained by performing 19 cycles of treatment with the coupling step, the oxidation step, and the deprotection step being defined as one cycle. Thus, theoretically, the $^{18}$O-labeled poly(U) had nineteen $^{18}$O atoms introduced thereto. Accordingly, it is calculated that the molecular weight of the $^{18}$O-labeled poly (U) increased by 38 (2×19 atoms), as compared with the molecular weight of unlabeled poly(U) (=6061.4). However, because the purity of the H$_2$$^{18}$O used was 99.2%, the actual increase in molecular weight was 2×19 atoms×(purity: 0.992)$^{19}$=32.6. Based on this, the theoretical molecular weight of the synthesized $^{18}$O-labeled poly(U) is 6061.4+ 32.6=6094.0. As described above, the observed value was 6094.2, which is very close to the theoretical molecular weight of 6094.0. Therefore, this result verifies that, by the present example, $^{18}$O atoms were introduced to phosphate groups in 19 phosphodiester bonds in the 20-mer poly(U).

(3) Evaluation of pH Stability

The pH stability of the obtained $^{18}$O-labeled poly(U) was evaluated. Specifically, the $^{18}$O-labeled poly(U) was mixed in a 50 mmol/l phosphate buffer solution at a predetermined pH (pH 3, 4, 5.5, 7, or 8.5) so that the concentration thereof was 20 µmol/1. The mixture was incubated at 37° C. for 28 days. Then, the stability of the $^{18}$O-labeled poly(U) after the incubation was examined by analyzing the molecular weight thereof using a LC-ESI-Q-Tof-MS (trade name: Waters SYNAPT G2 MS).

Figure 2:
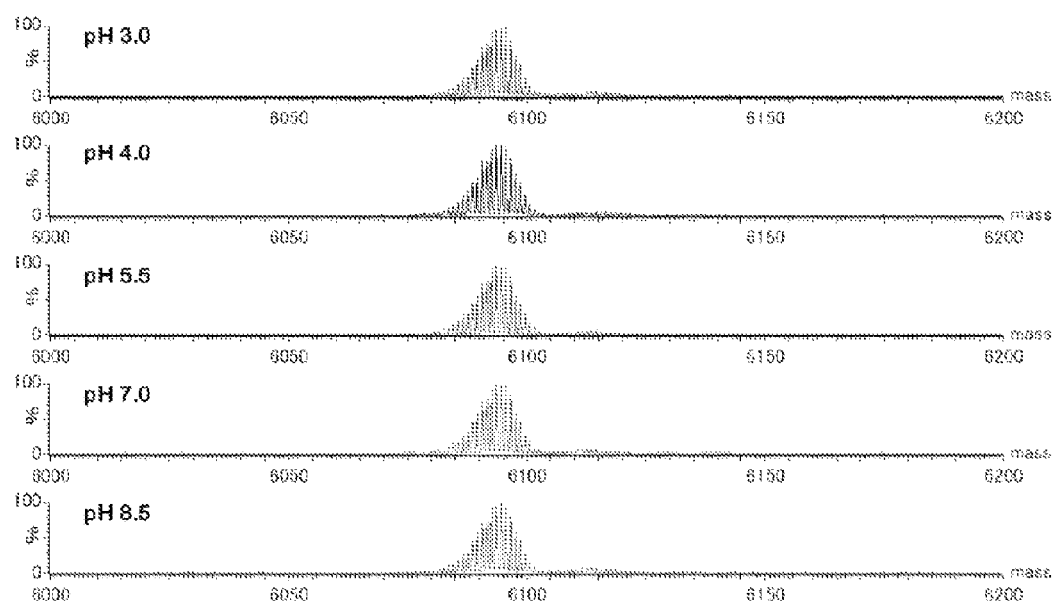
FIG. 2 shows mass spectrometry chromatograms of the $^{18}O$-labeled poly(U) treated at predetermined pHs in Example 1.

The results thereof are shown in FIG. 2. FIG. 2 shows chromatograms showing the results of mass spectrometry with respect to the $^{18}$O-labeled poly(U) after being incubated at the respective pHs. The graphs in FIG. 2 show, from the top, the results obtained after the $^{18}$O-labeled poly(U) had been treated at pH 3.0, 4.0, 5.5, 7.0, and 8.5. As shown in FIG. 2, the molecular weight of the $^{18}$O-labeled poly(U) before the incubation (the observed value: 6094.2) remained the same even after the treatment at the respective pHs. These results verify that the $^{18}$O-labeled poly(U) was stable at a pH in the range from 3 to 8.5. In other words, they verify that, at a pH in the range from 3 to 8.5, an $^{18}$O label is stable without being substituted with an ambient water molecule (H$_2$$^{16}$O). This demonstrates that an $^{18}$O label is stable also in in-vivo environments, so that the $^{18}$O label has a stability required for a tracer.

Example 2

(1) Synthesis of $^{18}$O Labeled siRNAs

According to the same RNA synthesis method as in Example 1, 21-mer RNAs represented by the following SEQ ID NOs: 1 to 4 were synthesized. The synthesized RNAs were subjected to 20 cycles of treatment, with the coupling step, the oxidation step, and the deprotection step being defined as one cycle. In all of these RNAs, a single $^{18}$O atom was introduced to each of phosphate groups in phosphodiester bonds by the RNA synthesis method. That is, twenty $^{18}$O atoms were introduced to each of the RNAs. On the other hand, RNAs represented by SEQ ID NOs: 1 to 4 were synthesized in the same manner, except that unlabeled H$_2$$^{16}$O was used as the oxidizing agent.

```
target sense RNA
                                (SEQ ID NO: 1)
5'-CCAUGAGAAGUAUGACAACAG-3' target antisense RNA
                                (SEQ ID NO: 2)
5'-GUUGUCAUACUUCUCAUGGUU-3' control sense RNA
                                (SEQ ID NO: 3)
5'-UACUAUUCGACACGCGAAGUU-3' control antisense RNA
                                (SEQ ID NO: 4)
5'-CUUCGCGUGUCGAAUAGUAUU-3'
```

The single-stranded RNAs having $^{18}$O introduced thereto were set to a target $^{18}$O-sense RNA, a target $^{18}$O-antisense RNA, a control $^{18}$O-sense RNA, and a control $^{18}$O-antisense RNA, respectively. Also, the single-stranded RNAs having $^{16}$O and not having $^{18}$O introduced thereto were set to a target $^{16}$O-sense RNA, a target $^{16}$O-antisense RNA, a control $^{16}$O-sense RNA, and a control $^{16}$O-antisense RNA, respectively.

(2) Measurement of Molecular Weight of Single-Stranded RNAs

The molecular weight of each of the thus-obtained single-stranded RNAs was measured in the same manner as in Example 1. In Table 1 below, the measured molecular weights (Observed mass) are shown together with the theoretical calculated values (Calculated mass). The theoretical calculated values were determined considering the fact that the $^{18}$O purity of the H$_2$$^{18}$O used was 99.2%.

TABLE 1

| RNA | Oxygen isotope | Calculated mass (Da)$^{(a)}$ | Observed mass (Da)$^{(b)}$ | Mass difference (Da)$^{(a-b)}$ |
|---|---|---|---|---|
| control sense RNA | $^{16}$O | 6656.99 | 6656.84 | −0.15 |
| | $^{18}$O | 6691.05 | 6691.80 | 0.75 |
| control antisense RNA | $^{16}$O | 6650.94 | 6650.71 | −0.23 |
| | $^{18}$O | 6685.00 | 6685.06 | 0.06 |
| target sense RNA | $^{16}$O | 6766.14 | 6765.96 | −0.18 |
| | $^{18}$O | 6800.20 | 6800.56 | 0.36 |
| target antisense RNA | $^{16}$O | 6588.86 | 6588.67 | −0.19 |
| | $^{18}$O | 6622.92 | 6622.97 | 0.05 |

As shown in Table 1, regarding each of the RNAs having $^{18}$O introduced thereto, it was found that the observed value was very close to the theoretical value. These results verify that, in the 21-mer RNAs having $^{18}$O introduced thereto, $^{18}$O was introduced to the phosphate group in each of twenty phosphodiester bonds.

The two bases (AG) at the 3' end of the target sense RNA and the two bases (UU) at the 3' end of the target antisense RNA were each an overhang sequence, and 19 bases excluding the overhang sequence in the target sense RNA were perfectly complementary to the same in the target antisense RNA. The following double strand composed of the target sense RNA and the target antisense RNA was siRNA against human GAPDH (target $^{18}$O-siRNA).

```
Target siRNA
                                      (SEQ ID NO: 1)
5' -CCAUGAGAAGUAUGACAACAG-3'

(SEQ ID NO: 2)
3' -UUGGUACUCUUCAUACUGUUG-5'
```

The two bases (UU) at the 3' end of the control sense RNA and the two bases (UU) at the 3' end of the control antisense RNA were each an overhang sequence, and 19 bases excluding the overhang sequence in the control sense RNA were perfectly complementary to the same in the control antisense RNA. A double strand composed of the control sense RNA and the control antisense RNA was siRNA (negative control $^{18}$O-siRNA) exhibiting no RNA interference ability against human GAPDH.

```
Control siRNA
                                      (SEQ ID NO: 3)
5' -UACUAUUCGACACGCGAAGUU-3'

(SEQ ID NO: 4)
3' -UUAUGAUAAGCUGUGCGCUUC-5'
```

(3) Evaluation of Purity of Each Single-Stranded RNA

The purity of each of the thus-obtained single-stranded RNAs was analyzed by HPLC under the following conditions. Assuming that the total peak area in the HPLC was 100%, the purity was represented as a proportion of a peak area at a retention time corresponding to the theoretical molecular weight of each of the single-stranded RNAs.

(HPLC Conditions)
analyzer: Shimadzu LC-10A system (Shimadzu Corporation)
column: XBridge OST C18, 2.5 μm (Waters)
column size: 4.6×50 mm
eluent:
 A: 50 mmol/l acetic acid triethylammonium salt (pH 7.4)+ 5% acetonitrile
 B: 50 mmol/l acetic acid triethylammonium salt (pH7.4)+ 50% acetonitrile
gradient: % B 5%→10%/20 min
flow rate: 1.0 ml/min
detector: UV detector (254 nm)

The results of the analysis are shown in Table 2 below. As shown in Table 2, the RNAs having $^{18}$O introduced thereto each exhibited a high purity, which was comparable to those of the $^{16}$O-RNAs not having $^{18}$O introduced thereto. These results verify that RNA labeled with $^{18}$O can be synthesized with the same yield and purity as RNA not having $^{18}$O introduced thereto.

TABLE 2

| RNA | Oxygen isotope | Amount (nmol)* | Purity (%) |
|---|---|---|---|
| control sense RNA | $^{16}$O | 473 | 89.1 |
|  | $^{18}$O | 484 | 87.5 |
| control antisense RNA | $^{16}$O | 425 | 75.3 |
|  | $^{18}$O | 443 | 74.5 |
| target sense RNA | $^{16}$O | 472 | 80.3 |
|  | $^{18}$O | 475 | 78.1 |
| target antisense RNA | $^{16}$O | 479 | 79.1 |
|  | $^{18}$O | 486 | 84.4 |

*the yield calculated from the absorbance at a wavelength of 260 nm (4) Formation of Double-Stranded RNAs By combining the thus-obtained single-stranded RNAs, double-stranded RNAs were formed in the following manner.

The two bases (UU) at the 3' end of the control sense RNA (SEQ ID NO: 3) and the two bases (UU) at the 3' end of the control antisense RNA (SEQ ID NO: 4) are each an overhang sequence, and 19 bases excluding the overhang sequence in the control sense RNA were perfectly complementary to the same in the control antisense RNA. A double strand composed of the control sense RNA and the control antisense RNA was siRNA exhibiting no RNA interference ability against human GAPDH.

```
Control siRNA
                                      (SEQ ID NO: 3)
5' -UACUAUUCGACACGCGAAGUU-3'

(SEQ ID NO: 4)
3' -UUAUGAUAAGCUGUGCGCUUC-5'
```

Thus, control siRNAs with the following combinations were formed.
(c1) the combination of the control $^{16}$O-sense RNA and the control $^{16}$O-antisense RNA ($^{16}$O/$^{16}$O)
(c2) the combination of the control $^{16}$O-sense RNA and the control $^{18}$O-antisense RNA ($^{16}$O/$^{18}$O)
(c3) the combination of the control $^{18}$O-sense RNA and the control $^{16}$O-antisense RNA ($^{18}$O/$^{16}$O)
(c4) the combination of the control $^{18}$O-sense RNA and the control $^{18}$O-antisense RNA ($^{18}$O/$^{18}$O)

On the other hand, two bases (AG) at the 3' end of the target sense RNA (SEQ ID NO: 1) and the two bases (UU) at the 3' end of the target antisense RNA (SEQ ID NO: 2) were each an overhang sequence, and 19 bases excluding the overhang sequence in the target sense RNA were perfectly complementary to the same in the target antisense RNA. The following double strand composed of the target sense RNA and the target antisense RNA was siRNA against human GAPDH.

```
Target siRNA
                                      (SEQ ID NO: 1)
5' -CCAUGAGAAGUAUGACAACAG-3'

(SEQ ID NO: 2)
3' -UUGGUACUCUUCAUACUGUUG-5'
```

Thus, target siRNAs with the following combinations were formed.
(t1) the combination of the target $^{16}$O-sense RNA and the target $^{16}$O-antisense RNA ($^{16}$O/$^{16}$O)
(t2) the combination of the target $^{16}$O-sense RNA and the target $^{18}$O-antisense RNA ($^{16}$O/$^{18}$O)
(t3) the combination of the target $^{18}$O-sense RNA and the target $^{16}$O-antisense RNA ($^{18}$O/$^{16}$O)
(t4) the combination of the target $^{18}$O-sense RNA and the target $^{18}$O-antisense RNA ($^{18}$O/$^{18}$O)

Then, the siRNAs (c1) to (c4) and (t1) to (t4) were applied to electrophoresis to determine the molecular weight of each of the siRNAs. The electrophoresis was carried out using 15% acrylamide gel.

Figure 3:
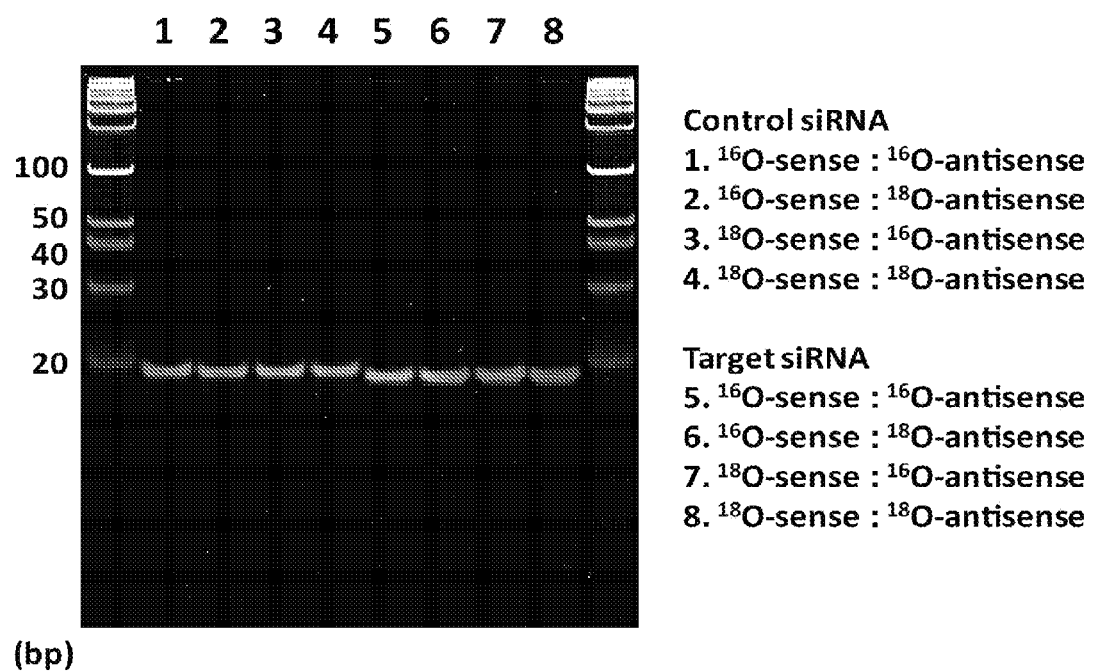
FIG. 3 is a Native-PAGE electrophoretogram of siRNAs each having $^{18}O$ introduced thereto in Example 2.

FIG. 3 shows the result of examining the formation of each double-stranded siRNAs. FIG. 3 shows Native-PAGE photographs for examining the formation of each siRNA. Lanes 1 to 4 show the results obtained regarding the control siRNAs (c1) to (c4), respectively, and Lanes 5 to 8 show the results obtained regarding the target siRNAs (t1) to (t4) respectively. As shown in FIG. 3, the control siRNAs shown in Lanes 1 to 4 exhibited molecular weights comparable to each other, and also, the target siRNAs shown in Lanes 5 to 8 exhibited molecular weights comparable to each other. These results demonstrate that RNA having $^{18}O$ introduced thereto forms a double strand to become siRNA, in a similar manner to RNA not having $^{18}O$ introduced thereto.

(5) Structure of siRNAs

Figure 4A:
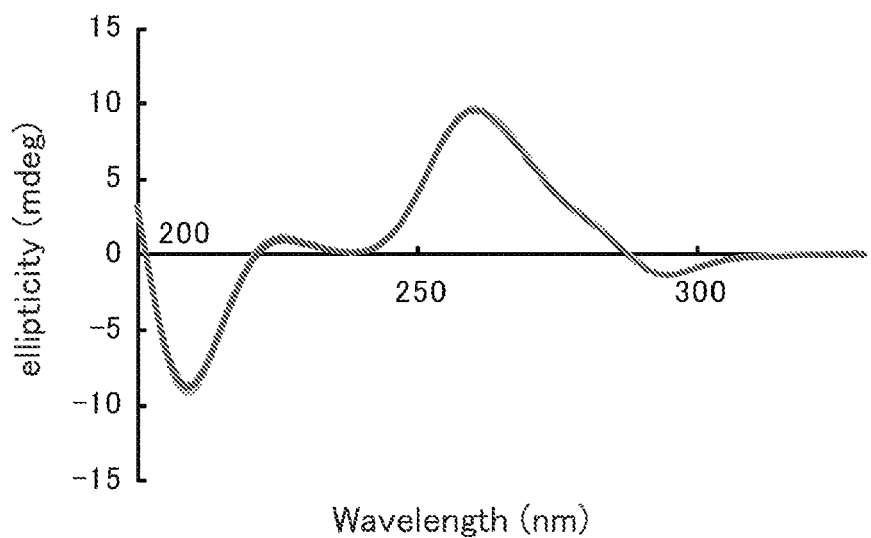
FIG. 4 shows graphs each showing a circular dichroism spectrum of siRNA having $^{18}O$ introduced thereto in Example 2.

Regarding the respective siRNAs described in the above item (4), their structures were compared with each other by circular dichroism spectrometry (CD spectrometry). The measurement was carried out using a spectropolarimeter (trade name: J-720 W, JASCO International Co., Ltd.). FIG. 4 shows the results of the CD spectrometry. Among the siRNAs (c1) to (c4) and (t1) to (t4), the results obtained regarding the control siRNA (c4) ($^{18}O/^{18}O$) and the target siRNA (t4) ($^{18}O/^{18}O$) are shown in FIG. 4. In FIG. 4, the vertical axis indicates the ellipticity (molecular ellipticity) (millidegree: mdeg), and the horizontal axis indicates the wavelength (nm). FIG. 4A shows the results obtained regarding the control siRNA (c4) ($^{18}O/^{18}O$), and FIG. 4B shows the results obtained regarding the target siRNA (t4) ($^{18}O/^{18}O$).

Figure 4B:
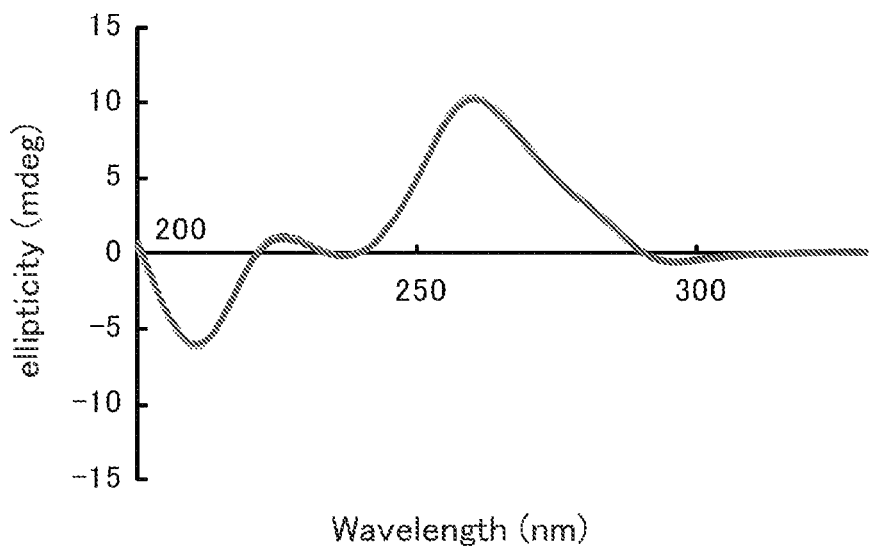

The control siRNAs (c1) to (c3) (not shown) all exhibited the same CD spectra as the control siRNA (c4) shown in FIG. 4A, and the target siRNAs (t1) to (t3) (not shown) all exhibited the same CD spectra as the target siRNA (t4) shown in FIG. 4B. These results verify that the four kinds of control siRNAs had the same structure, and that the four kinds of target siRNAs had the same structure. In other words, it was verified that siRNA having $^{18}O$ introduced thereto has the same structure as siRNA not having $^{18}O$ introduced thereto.

(6) Thermodynamic Stability of siRNAs

The thermodynamic stability of each of the siRNAs described in the above item (4) was examined. The thermodynamic stability (Tm value) was measured by a spectrophotometer (trade name: UV-1800 UV-VIS, Shimadzu Corporation).

Table 3 below shows the results of examining the thermodynamic stability. As shown in Table 3, regarding the target siRNAs, it was found that the respective siRNAs exhibited substantially the same thermodynamic stability. Also, regarding the control siRNAs, it was found that the respective siRNAs exhibited substantially the same thermodynamic stability. These results demonstrate that the thermodynamic stability of siRNA having $^{18}O$ introduced thereto is comparable to siRNA not having $^{18}O$ introduced thereto.

TABLE 3

| Combination of RNAs | Control siRNA | Target siRNA |
|---|---|---|
| $^{16}O$-sense RNA<br>$^{16}O$-antisense RNA | 67.69 | 67.16 |
| $^{16}O$-sense RNA<br>$^{18}O$-antisense RNA | 67.52 | 67.25 |
| $^{18}O$-sense RNA<br>$^{16}O$-antisense RNA | 67.20 | 66.66 |
| $^{18}O$-sense RNA<br>$^{18}O$-antisense RNA | 67.10 | 66.66 |

(7) Biological Activity of siRNAs

The expression-inhibiting ability of each of the siRNAs described in the above item (4) was examined by measuring the mRNA expression level of the human GAPDH gene.

As cells, HCT 116 cells (derived from human colon adenocarcinoma) were used. The culture conditions were 37° C. and 5% $CO_2$. As a medium, a McCoy's 5A medium containing 10% inactivated calf serum was used.

First, the cells were cultured in the medium, and the resultant liquid culture was dispensed to a 24-well plate so that each well contained 400 µl of the medium to achieve a density of $4 \times 10^4$ cells/well. Thereafter, the cells were transfected with the siRNA using a transfection reagent (trade name: Lipofectamine 2000, Invitrogen) in accordance with the protocol attached thereto. More specifically, 100 µl of a complex of the siRNA and the transfection reagent were added per well. Thus, the total amount in each well was 500 µl, and the final concentration of the siRNA was 0.1 nmol/l.

After the transfection, the cells were cultured for 24 hours. Then, RNA was collected using a reagent (trade name: RNeasy Mini Kit, Qiagen) in accordance with the protocol attached thereto. Thereafter, cDNA was synthesized from the RNA using a reverse transcriptase (trade name: SuperScript III, Invitrogen) in accordance with the protocol attached thereto. Then, PCR was carried out with the thus-obtained cDNA as a template, and the expression level of mRNA of the human GAPDH gene and the expression level of the β-actin gene as the internal standard were measured. The expression level of the human GAPDH gene was corrected with the expression level of the β-actin gene. In the PCR, the GAPDH gene and the β-actin gene were amplified using the following primer sets, respectively. The expression level of the human GAPDH gene was determined as a relative value, assuming that the expression level of the human GAPDH gene in cells to which the siRNA had not been added was 1.

```
Primer set for GAPDH gene amplification
                                        (SEQ ID NO: 5)
5'-GGAGAAGGCTGGGGCTCATTTGC-3'

(SEQ ID NO: 6)
5'-TGGCCAGGGGTGCTAAGCAGTTG-3'

Primer set for β-actin gene amplification
                                        (SEQ ID NO: 7)
5'-GCCACGGCTGCTTCCAGCTCCTC-3'

(SEQ ID NO: 8)
5'-AGGTCTTTGCGGATGTCCACGTCAC-3'
```

As control 1, the gene expression level also was measured in cells to which the siRNA and the transfection reagent had not been added (−). As control 2, the gene expression level also was measured in cells to which the siRNA had not been added and only the transfection reagent had been added in the transfection step (mock).

Figure 5:
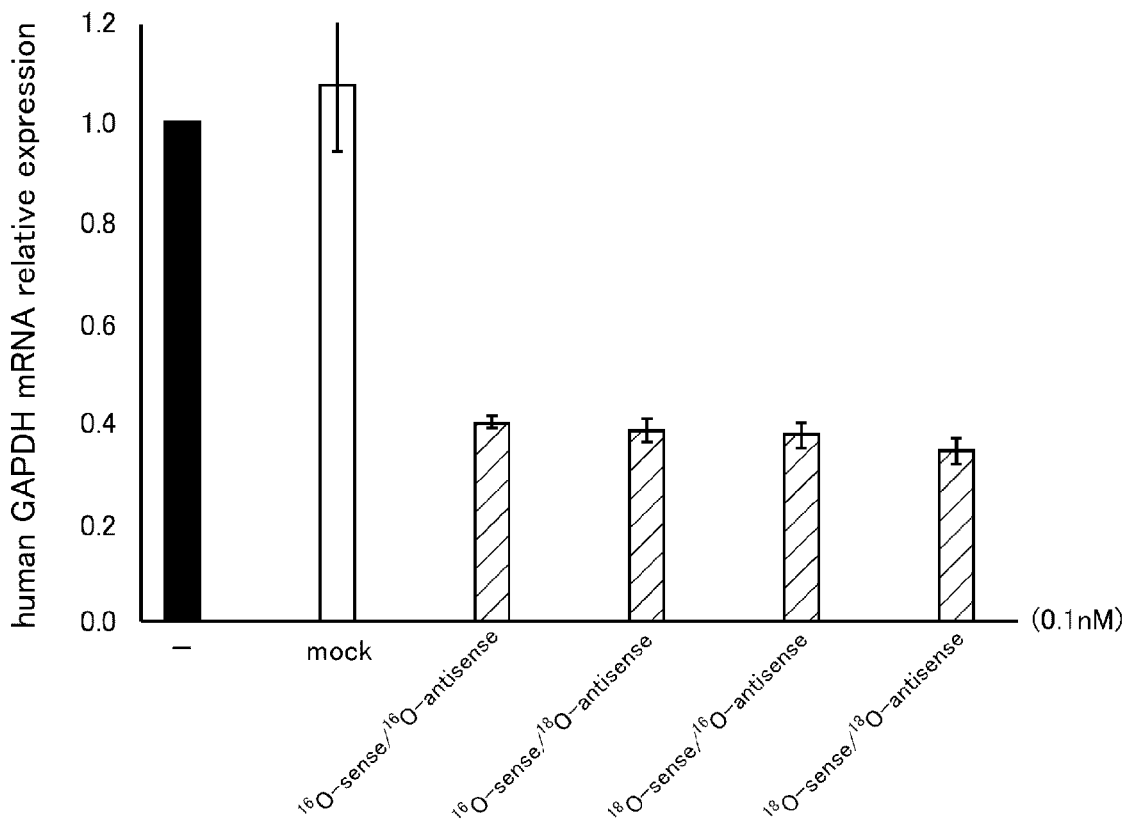
FIG. 5 is a graph showing the relative mRNA expression levels of the human GAPDH gene in Example 2.

The results thereof are shown in FIG. 5. FIG. 5 is a graph showing the relative expression level of mRNA of the human GAPDH gene. In FIG. 5, the vertical axis indicates the relative gene expression level. As shown in FIG. 5, the target siRNAs having $^{18}O$ introduced thereto all exhibited substantially the same expression-inhibiting activity as the target siRNA not having $^{18}O$ introduced thereto. These results verify that siRNA having $^{18}O$ introduced thereto can be used in a similar manner as siRNA having $^{16}O$ and not having $^{18}O$ introduced thereto.

Example 3

The concentration of the $^{18}O$-labeled poly(U) synthesized in Example 1 in serum was measured.

Serum samples were prepared by adding the $^{18}O$-labeled poly(U) to pooled mouse serum at predetermined concentrations. The predetermined concentrations were 0, 0.01, 0.02, 0.04, 0.06, 0.08, 0.1, 0.2, 0.4, 0.6, 0.8, 1, and 2 μg/ml. Each serum sample was placed in a silver capsule and lyophilized. Then, the lyophilized serum sample was supplied to a stable isotope ratio mass spectrometer connected to a gasification pretreatment device. As the gasification pretreatment device, a TC/TA manufactured by Thermo Fisher Scientific was used. As the stable isotope ratio mass spectrometer, a VELTA V Plus manufactured by Thermo Fisher Scientific was used. Then, the measured value of the serum sample was substituted into the following equation to determine $\delta^{18}O$ (permillage: ‰). In the following equation, R(s) is the measured value of the $^{18}O/^{16}O$ ratio of the serum sample, and R(r) is the measured value of the $^{18}O/^{16}O$ ratio of the reference material.

$$\delta^{18}O(‰)=[R(s)/R(r)-1]\times 1000$$

Figure 6:
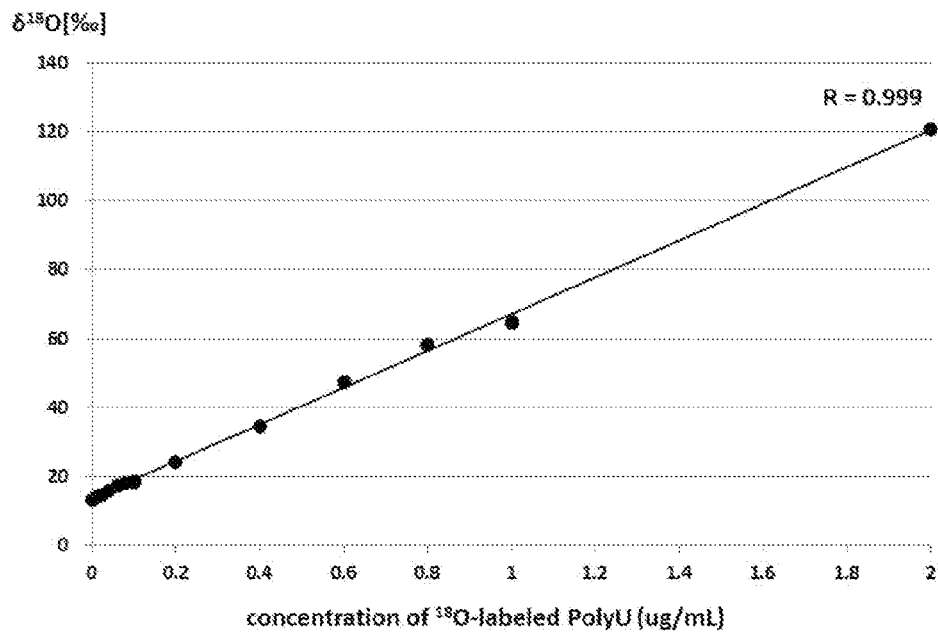
FIG. 6 is a graph showing the relationship between the concentration of $^{18}O$-labeled poly(U) and $\delta^{18}O$ rod in Example 3.

FIG. 6 is a graph showing the correlation between the $\delta^{18}O$ value and the concentration of the $^{18}O$-labeled poly(U). In FIG. 6, the vertical axis indicates the $\delta^{18}O$ value (‰), and the horizontal axis indicates the concentration of the $^{18}O$-labeled poly(U). As can be seen from FIG. 6, the $\delta^{18}O$ value and the concentration of the $^{18}O$-labeled poly(U) exhibited a positive correlation, and the correlation was very high with the correlation coefficient (R) being 0.999.

Conventional methods for measuring the concentration of RNA in blood involve the use of radioisotope-labeled RNA. However, radioisotopes raise fears of exposure to radiation. In contrast, in the present example, the RNA having the stable isotope $^{18}O$ introduced thereto was used, and as can be seen from FIG. 6, it was verified that, even in the case where the $^{18}O$-labeled RNA was used, there was a correlation between the RNA concentration and the $\delta^{18}O$ value (‰) in blood. This demonstrates that, by using RNA having $^{18}O$ introduced thereto as RNA for use in a pharmaceutical or the like, it is possible to measure the concentration of the RNA in blood after it is administered to a living organism while ensuring the safety, for example.

Example 4

Regarding the siRNA having $^{18}O$ introduced thereto synthesized in Example 2, intracellular localization thereof was observed using a stable isotope microscope.

(1) siRNA

The siRNA used was the control siRNA (c4) ($^{18}O/^{18}O$) obtained by combining the $^{18}O$-sense RNA and the $^{18}O$-antisense RNA prepared in Example 2.

(2) Sample Preparation

A 7 mm×7 mm silicon wafer was placed at the center of each of 35 mm dishes. Human lung-derived A549 cells were seeded in the respective dishes at a density of $5\times10^5$ cells/dish and then cultured. The culture conditions were 37° C., 5% $CO_2$, and 24 hours. The medium used was a 10% FCS-containing Dulbecco's modified eagle medium (DMEM) (Sigma). After the culture, the medium was replaced with 2 ml of a fresh medium. Then, siRNA was added so that the final concentration thereof was 300 nmol/l, and the cells were transfected with the siRNA using a transfection reagent (trade name: Lipofectamine 2000, Invitrogen). After the transfection, the cells were cultured for another 24 hours. The cultured cells were washed with PBS. Then, the cells were treated with a 2.5% glutaraldehyde-PBS solution at 37° C. for 1 hour, thereby immobilizing the cells. Thereafter, the immobilized cells were dehydrated by immersing them in 20%, 40%, 60%, 70%, 80%, 90%, and 100% ethanols in this order for 10 minutes each. Tert-butanol was added to the dehydrated cells, and the cells were frozen in a freezer and then dried. The thus-obtained lyophilizate was coated with gold with a coating thickness of 30 nm. Thus, a sample was prepared.

(3) Observation with Stable Isotope Microscope

Figure 7:
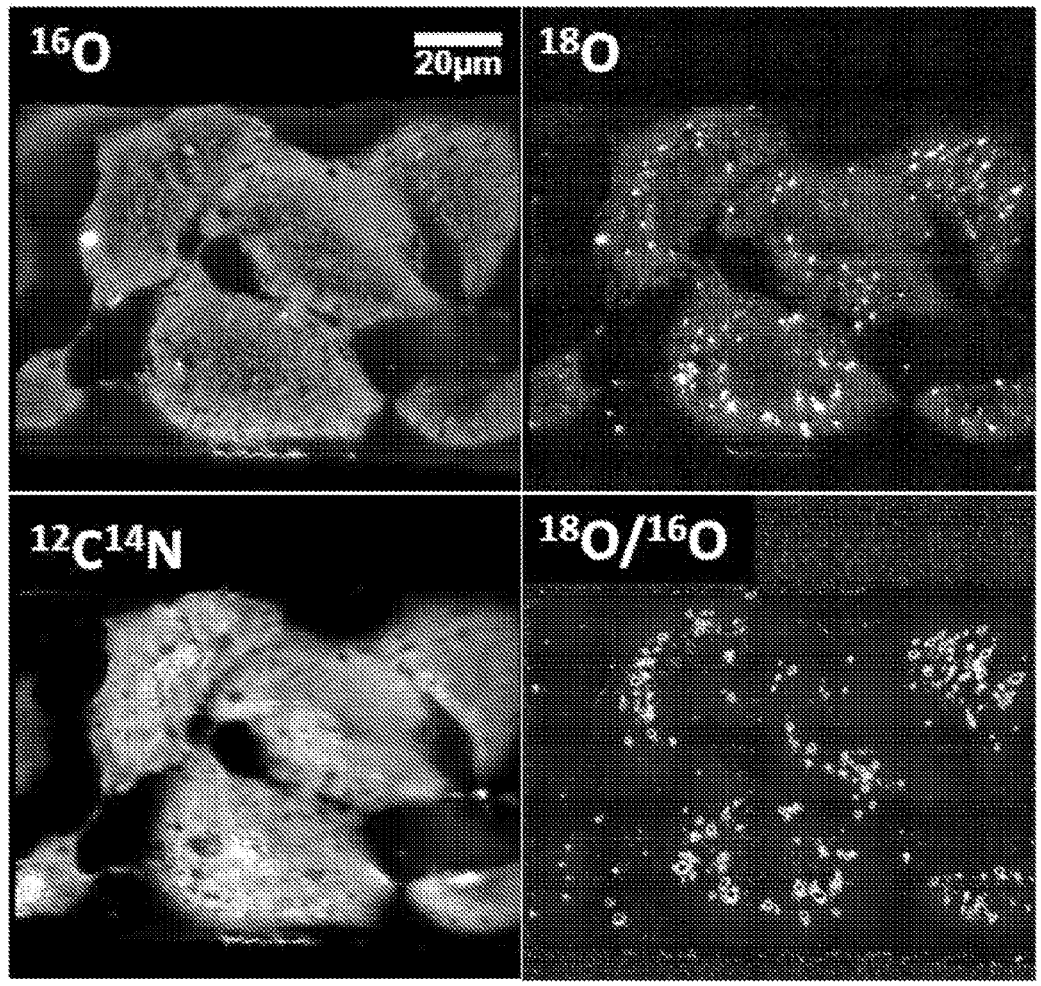
FIG. 7 shows photographs showing the results of observation of intracellular localization of siRNA having $^{18}O$ introduced thereto in Example 4.

The sample was observed with a stable isotope microscope system (Hokkaido University, Cameca ims-1270+SCAPS). In the observation, cesium was used as a primary beam, and secondary ion images of $^{12}C^{14}N$, $^{16}O$, and $^{18}O$ were obtained. The results of this observation are shown in FIG. 7. FIG. 7 shows micrographs showing the result of observing the intracellular localization of the control siRNA ($^{18}O/^{18}O$). In FIG. 7, the upper left photograph is the secondary ion image of $^{16}O$, the lower left photograph is the secondary ion image of $^{12}C^{14}N$, the upper right photograph is the secondary ion image of $^{18}O$, and the lower right photograph is the secondary ion image of $^{18}O/^{16}O$.

The secondary ion image of $^{12}C^{14}N$ resulted from the imaging of organic substances, so that the shapes of the cells can be observed in the lower left photograph ($^{12}C^{14}N$) in FIG. 7. In secondary ion images of $^{16}O$, portions where the intensity of $^{16}O$ is high are seen as white, whereas portions where the intensity of $^{16}O$ is low are seen as black. The upper left photograph ($^{16}O$) in FIG. 7 is entirely blackish, from which it was found that natural $^{16}O$ were presence evenly. In secondary ion images of $^{18}O$, portions where the intensity of $^{18}O$ is high are seen as white, whereas portions where the intensity of $^{18}O$ is low are seen as black. In the upper right photograph ($^{18}O$) of FIG. 7, many white dots are seen in regions corresponding to cytoplasms, from which it was found that the administered control siRNA ($^{18}O/^{18}O$) was localized in the cytoplasms. Next, a secondary ion image of $^{18}O/^{16}O$ results from imaging of the state where a secondary ion image of $^{18}O$ (the intensity of $^{18}O$) is divided with a secondary ion image of $^{16}O$ (the intensity of $^{16}O$), and portions where the ratio of $^{18}O$ is low are seen as blue, whereas portions where the ratio of $^{18}O$ is high are seen as red. In the lower right photograph ($^{18}O/^{16}O$) of FIG. 7, the ratio of $^{18}O/^{16}O$ was high in portions corresponding to the white dots in the upper right photograph ($^{18}O$), so that the portions are seen as red (white dots in the photograph). The ratio of $^{18}O/^{16}O$ in other portions was around 0.002, which corresponds to a naturally-occurring $^{18}O/^{16}O$ ratio, so that the portions are seen as blue. From these results, it was found that, by using siRNA having $^{18}O$ introduced thereto, an image showing the localization of the siRNA can be obtained based on the $^{18}O/^{16}O$ ratio without using a fluorescence label or the like, for example.

Heretofore, fluorescently-labeled nucleic acids generally are used for imaging. However, fluorescent substances usually are hydrophobic and have high molecular weights. Thus, when a fluorescent substance is added to an end or the like of a nucleic acid, the nucleic acid might exhibit different physical properties than when it is not modified by being labeled with the fluorescent substance. Furthermore, there is a possibility that the fluorescent substance might be cleaved in vivo. In contrast, labeling with $^{18}O$ is advantageous in that, for example: the change in physical properties of a nucleic acid can be suppressed; $^{18}O$ can modify all the phosphate groups; and the cleavage of the modification can be suppressed. Thus, by using a nucleic acid having $^{18}O$ introduced thereto, it becomes possible to observe intracellular localization more efficiently, for example.

While the present invention has been described above with reference to illustrative embodiments, the present invention is by no means limited thereto. Various changes and modifications that may become apparent to those skilled in the art may be made in the configuration and specifics of the present invention without departing from the scope of the present invention.

This application claims priority from Japanese Patent Application No. 2011-105722 filed on May 10, 2011. The entire disclosure of this Japanese Patent Application is introduced herein by reference.

INDUSTRIAL APPLICABILITY

As specifically described above, according to the preparation process of the present invention, an isotope-containing phosphate compound can be prepared easily merely by using the oxidizing agent containing the isotope. The preparation process of the present invention is useful in, for example, synthesis of nucleic acids having a phosphate group(s) and synthesis of low molecular weight compounds having a phosphate group(s), such as agricultural chemicals, pharmaceuticals, and phospholipids.

The invention claimed is:

1. A process for preparing an isotope-containing phosphate compound, the process comprising the step of:
oxidizing a trivalent phosphorus compound with an oxidizing agent containing an isotope to synthesize a pentavalent phosphate compound to which the isotope has been introduced,
wherein
the oxidizing agent containing an isotope is (a) $I_2$/water containing $^{17}O$ or $^{18}O$ or (b) a peroxide containing $^{17}O$ or $^{18}O$, and
the trivalent phosphorus compound is a compound that includes the structure

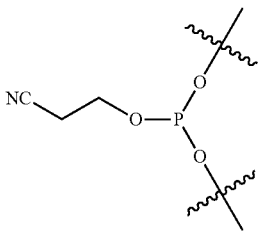

2. The process according to claim 1, wherein
the oxidation reaction caused by the oxidizing agent is such that trivalent phosphorus in the trivalent phosphorus compound is oxidized to pentavalent phosphorus and an atom derived from the oxidizing agent then binds to the pentavalent phosphorus, and
the oxidizing agent contains the isotope as the atom binding to the pentavalent phosphorus.

3. The process according to claim 1, wherein the oxidizing agent containing an isotope is a peroxide containing $^{17}O$ or $^{18}O$.

4. The process according to claim 3, wherein the peroxide is a hydroperoxide.

5. The process according to claim 4, wherein the hydroperoxide is t-butyl hydroperoxide.

6. The process according to claim 1, wherein the trivalent phosphorus compound is a phosphorous ester.

7. The process according to claim 1, wherein
the trivalent phosphorus compound is a monomer containing a nucleoside having the trivalent phosphorus,
the nucleoside contains a sugar and a base with the base being bound to the 1'-position of the sugar, and
the trivalent phosphorus is bound to the sugar.

8. The process according to claim 7, wherein the trivalent phosphorus is bound to the 5'-, 3'-, or 2'-position of the sugar.

9. The process according to claim 1, wherein
the trivalent phosphorus compound is a polymer containing two or more nucleoside residues, each of the nucleoside residues contains a sugar and a base with the base being bound to the 1'-position of the sugar,
between the adjacent nucleoside residues, sugars in the respective nucleoside residues are bound to each other via phosphorus,
phosphorus between at least one pair of adjacent nucleoside residues is the trivalent phosphorus.

10. The process according to claim 9, wherein between the adjacent nucleoside residues, the 5'-, 3'-, or 2'-position of one of the sugars is bound to the 5'-, 3'-, or 2'-position of the other sugar via the phosphorus.

11. The process according to claim 1, further comprising a coupling step of coupling two molecules of monomers each containing a nucleoside to synthesize the trivalent phosphorus compound, wherein
in the oxidation step, the trivalent phosphorus compound obtained by the coupling step is oxidized with the oxidizing agent to synthesize a pentavalent phosphate compound to which the isotope has been introduced.

12. The process according to claim 1, further comprising a coupling step of coupling a monomer containing a nucleoside to the pentavalent phosphate compound to synthesize the trivalent phosphorus compound, wherein in the oxidation step, the trivalent phosphorus compound obtained by the coupling step is oxidized with the oxidizing agent to synthesize a pentavalent phosphate compound to which the isotope has been introduced.

13. The process according to claim 1, wherein the pentavalent phosphate compound is an agricultural chemical, a pharmaceutical, or a phospholipid.

* * * * *